(12) United States Patent
Gräter et al.

(10) Patent No.: US 7,746,229 B2
(45) Date of Patent: Jun. 29, 2010

(54) DEVICE AND METHOD FOR IDENTIFYING, LOCATING AND TRACKING OBJECTS ON LABORATORY EQUIPMENT

(75) Inventors: Matthias Gräter, Uetikon (CH); Nikolaus Ingenhoven, Uerkion (CH)

(73) Assignee: Tecan Trading AG, Mannedorf (CH)

( * ) Notice: Subject to any disclaimer, the term of this patent is extended or adjusted under 35 U.S.C. 154(b) by 511 days.

(21) Appl. No.: 11/547,597

(22) PCT Filed: Mar. 30, 2005

(86) PCT No.: PCT/CH2005/000183

§ 371 (c)(1), (2), (4) Date: Nov. 3, 2006

(87) PCT Pub. No.: WO2005/098455

PCT Pub. Date: Oct. 20, 2005

(65) Prior Publication Data

US 2008/0042839 A1 Feb. 21, 2008

(30) Foreign Application Priority Data

Apr. 28, 2004 (CH) .......... 748/04

(51) Int. Cl.
G08B 13/14 (2006.01)
(52) U.S. Cl. ............ 340/572.1; 340/10.1; 340/10.5
(58) Field of Classification Search .......... 340/572.1, 340/505
See application file for complete search history.

(56) References Cited

U.S. PATENT DOCUMENTS

| | | | | |
|---|---|---|---|---|
| 5,874,724 A | * | 2/1999 | Cato | 235/492 |
| 6,127,928 A | * | 10/2000 | Issacman et al. | 340/572.1 |
| 6,812,838 B1 | * | 11/2004 | Maloney | 340/568.1 |
| 7,002,473 B2 | * | 2/2006 | Glick et al. | 340/572.1 |
| 7,049,961 B2 | * | 5/2006 | Maloney | 340/568.1 |
| 7,323,989 B2 | * | 1/2008 | Allen | 340/572.1 |
| 7,350,715 B2 | * | 4/2008 | Pradhan et al. | 235/492 |
| 7,420,468 B2 | * | 9/2008 | Fabian et al. | 340/572.1 |
| 7,492,257 B2 | * | 2/2009 | Tethrake et al. | 340/572.1 |
| 2005/0024211 A1 | * | 2/2005 | Maloney | 340/572.1 |
| 2006/0145856 A1 | * | 7/2006 | Tethrake et al. | 340/572.1 |
| 2008/0088454 A1 | * | 4/2008 | Flores et al. | 340/572.4 |
| 2008/0117053 A1 | * | 5/2008 | Maloney | 340/572.4 |

* cited by examiner

Primary Examiner—Travis R Hunnings
(74) Attorney, Agent, or Firm—Notaro, Michalos & Zaccaria P.C.

(57) ABSTRACT

The invention concerns a system (1) to locate or track objects (2) that can be positioned on the work table (3) of a laboratory apparatus (4). To do this, the system (1) comprises at least:
a) a central transmitter (5) with the capability to transmit and receive radio frequency (RF) signals, convert RF signals received and transfer the converted signals to a computer (7);
b) a local unit (6) mounted on a surface (8) of the work table (3) with the capability to receive and transmit RF signals;
c) radio frequency identification (RFID) tags (10) to be affixed to the local unit (6) and to articles of laboratory ware (15) that are to be identified and/or located or tracked;
d) a work table (3) of a laboratory apparatus (4) and a computer (7) that can be connected to the laboratory apparatus (4) and is linked to the central transmitter (5) via an interface, the computer (7) having the capability to communicate with the central transmitter (5), to process signals received from the latter and to address selected RFID tags (10) through the central transmitter (5).

Figure 1:
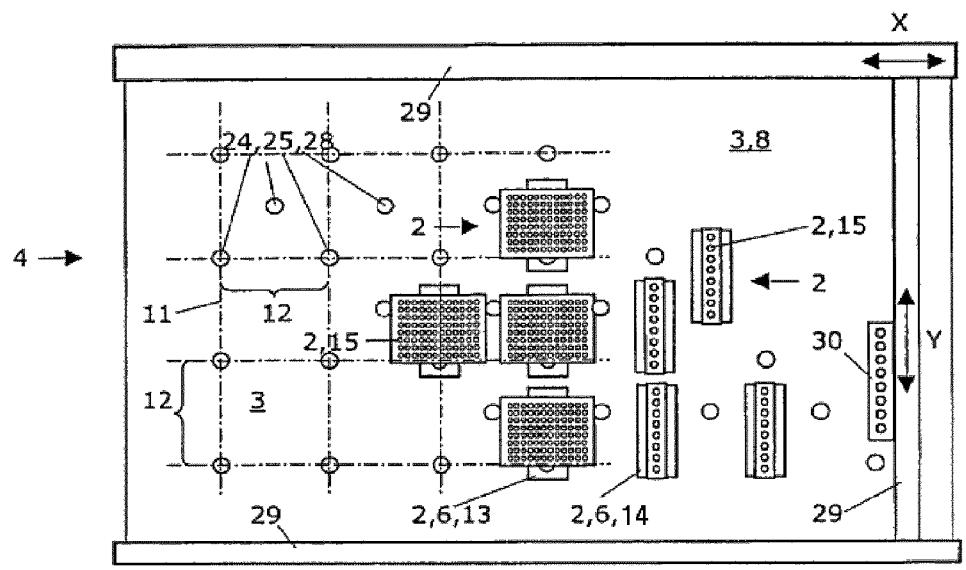

The system (1) according to the invention can be integrated in a higher-ranking logistical system (31) for the processing and analysis of samples of any desired kind.

19 Claims, 2 Drawing Sheets

Fig. 3A
Fig. 3B
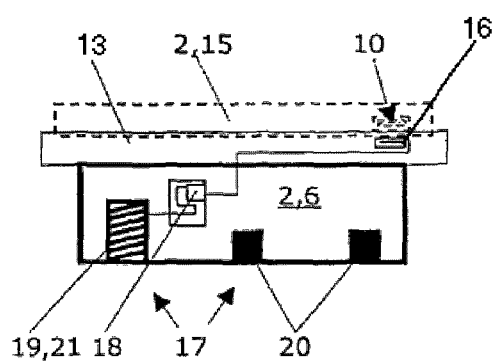
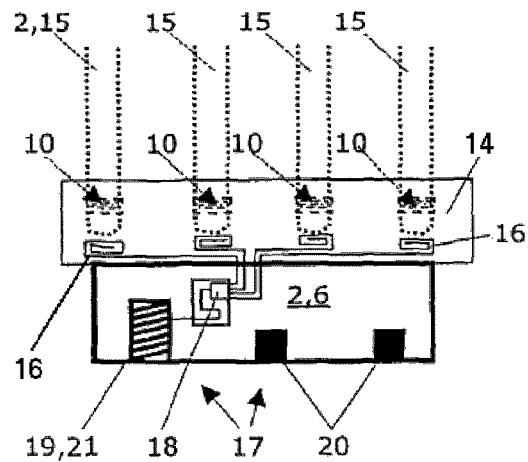
Fig. 4A
Fig. 4B
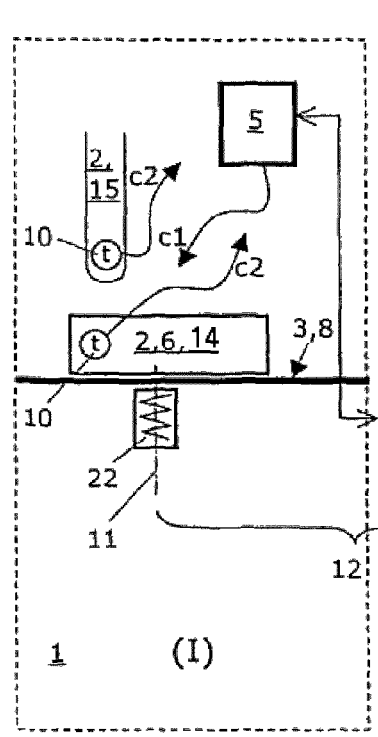
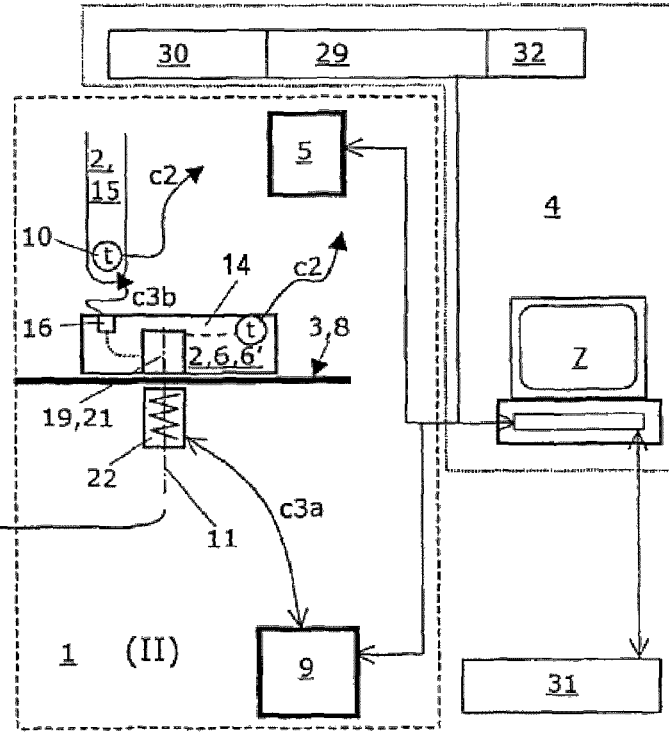

DEVICE AND METHOD FOR IDENTIFYING, LOCATING AND TRACKING OBJECTS ON LABORATORY EQUIPMENT

The present invention concerns a device and procedure to identify, locate and track objects on laboratory apparatus by the use of a computer controlled radio frequency identification (RFID) system and radio frequency identification labels or "RFID tags", which are attached to such objects.

The most diverse branches of industry demand automated systems for moving goods on or between workstations. More specifically, this concerns positioning systems for the precise placing of goods at each workstation that comprises a device for manipulating the goods at a specific workstation. For example, in pharmaceutical research or clinical diagnosis, several types of automated systems are used. In both these cases, this concerns conventional installations, which basically always consist of a variant on a procedure for moving fluids or dry preparations from one container to another. In addition, these preparations are examined or processed by known methods, such as optical measurements, transfer by pipette, washing, incubation and filtering.

Such known automatic systems are similar insofar as the transfer and manipulation of samples are performed by means of "workstations", as they are called, or special apparatus. These workstations may be operated individually by hand or connected together into an automated system. With automatic systems, the user does not have to carry out or provide for all the individual methods of processing. Another common factor uniting such known systems lies in the fact that samples are often processed in standardised microplates. Such microplates can be obtained in every possible format, but typically comprise 96 sample containers or "wells" arranged in a regular 8×12 raster with an interval of 9 mm between centres. Microplates with a multiple, or even only a part, of this number of wells are also used. Different workstations may be connected to one or more robots to carry the microplates. One or more robots moving in accordance with the system of Cartesian coordinates may be used on a workbench top. These Cartesian robots can carry plates or other sample containers and also transfer fluids. A central control system or computer monitors and controls these known systems, the outstanding advantage of which lies in the complete automation of work processes. As a consequence, such systems can be operated for hours or days on end, without the need for any human intervention.

The use of "plate stackers", as they are called, makes the use of another kind of robot possible. Thus, for example, a loading stacker can be positioned on one side of a piece of apparatus, such as a liquid handling system or an optical plate scanning device, and an output stacker on the other side. Microplates can then be introduced into the input zone of the loading stacker by a conveyor belt or robot arm, e. g. a "pick-and-place arm". On completion of a process step by the automatic system, the microplate is accordingly deposited on the input zone of the output stacker. Such stackers often use removable cassettes, so that approximately 20 microplates can be moved from one system to another all at once. This is usually done manually or by means of a jointed-arm robot for the transfer of stacks between workstations. The samples can be incubated by simply inserting a whole stack into the incubator. Plate stackers can also be combined with conventional workstations.

There is a need in the most diverse branches of the automation industry, whether this concerns pharmaceutical research, clinical diagnosis or even the manufacture of such products, for a device or procedure to locate and track objects on laboratory apparatus. This need particularly concerns a system or procedure to locate and track objects on a work table of a workstation for the liquid handling of samples.

From U.S. Pat. No. 6,429,016 a system and procedure are known for positioning a sample or a charge in relation to a specific device in an automatic system. A two-part installation is disclosed, which employs a "macro-positioning system" for larger sample movements between workstations and a "micro-positioning system" for the precise positioning of samples. The "macro-positioning system" is based on robots which move on or along a system of tracks or rails while carrying sample containers, e. g. a microplate. At a desired workstation, the subordinate "micro-positioning system" intervening each time between the workstation and a sample holder provides for precise positioning of the samples in a predetermined place on the workstation. This place corresponds with the equipment of a device (e. g. a pipetting or dispensing device) which is used to interact with the samples or carry out specific tasks on the latter. When a robot reaches its prescribed destination, it is there identified and checked to see whether it is in the right position. This can be done using a two-way infrared link, a proximity radio frequency, radio frequency identification (RFID), electrical contacts or a one or two-dimensional barcode. The complexity of this system is based at least partly on a number of object-carrying robots, each one with its own autonomous navigation system. Limits are imposed on this system by the fact that the robots move along a system of tracks on the surface of a work table. This means that at least a large part of the area occupied by this track system is inaccessible because it is a "traffic area" and is not available for the processing of samples.

A procedure and device to locate and track documents and other objects are known from U.S. Pat. No. 6,127,928. This discloses a radio frequency control system capable of finding the storage location of documents, such as office files and similar, automatically and fast. A central transmitter controlled by a personal computer (PC) sends a coded radio frequency signal (RF signal) on a first frequency to cheaply produced, addressable local transmitter/receivers, positioned in a bookcase or in drawers. These local, also sequentially addressable transmitters, relay the coded RF signal on a second frequency via an antenna. A passive radio frequency identification (RFID) tag, containing the same code as that relayed by the local transmitter, is affixed to a filing cabinet, for example and, if it is in proximity to the antenna of the local transmitter, receives energy from the RF field generated by the local transmitter. This activated RFID tag now modulates the RF signal on the second frequency whereupon this modulated signal is received by the central transmitter. Through a PC coupled to a central transmitter, the system is now enabled to perform the location of an RFID labelled document folder automatically and quickly down to a particular drawer or a particular bookcase shelf in an office environment. However, a specialist will perceive no way in which this system could be adapted to identify, locate and track objects on laboratory apparatus.

It was therefore a task of the present invention to propose an alternative system and procedure to identify, locate and track objects on laboratory apparatus. It was a further task of the present invention to propose a system and procedure to identify, locate and track objects on laboratory apparatus that would also be simple in its functioning and use. Another task of the present invention was to propose a system and procedure to identify and locate or track objects on laboratory apparatus that would not occupy any of the working surface as a traffic area.

The solution to these and other tasks is provided by the characteristics of the independent claims. Preferred improvements and additional characteristics of the invention will become apparent from the dependent claims.

The present invention is based on the following concept:

All objects to be placed on the work table of a laboratory apparatus, e. g. modules, carriers and articles of laboratory ware are first of all equipped with a radio frequency identification (RFID) label, or RFID tag. The system according to the invention provides means to activate these RFID tags and to receive the RF signals transmitted by these RFID tags.

Instead of a location identifying system (in all probability much more expensive) comprising a three-dimensional arrangement of at least three RFID tag scanner devices and the identification of the RFID tags by means of time-based interrogation and 3-D triangulation, a simpler system is proposed which combines general excitation with location-based excitation followed in each case by acquisition of the RFID tags present. The strategy proposed is thus outstandingly well suited to facilitating robust, location-based tag identification.

Means are provided which are configured to activate all the RFID tags present, so that all the RF signals from these tags can be collected and listed in groups according to the type of object labelled. Means are also provided which are configured in such a way that each RFID tag that is present on the work table can be individually activated, so that the current position of each RFID tag in a coordinate grid on the work table of the system can be detected.

Advantages offered by the invention include:
1. the acquisition of possible faulty positioning of carriers or racks on the surface of a work table, the faulty positioning being detected independently of the movements or coordinate system of a robot;
2. the acquisition of possible faulty positioning of general laboratory equipment, e. g. microplates or sample tubes on the carriers or racks;
3. the production of lists of positions and movements corresponding to the acquisition of possible faulty positioning of carriers or racks (cf. 1.) and the acquisition of possible faulty positioning of general laboratory articles (cf. 2.), these lists being drawn up independently of the movements or the coordinate system of a robot and representing a true indication of their actual positions;
4. integration of the distribution according to 3. into higher-ranking logistical systems, which may comprise, for example, chemical libraries, stackers, incubators, analysis machines, centrifuges, imaging systems, etc.;
5. Precise fixing of microplate carriers and tube racks on a smooth work table surface, if mechanical fixing elements are not used;
6. The possibility of using a completely flat, smooth work table surface, needing only cleaning and disinfection, if mechanical fixing elements are not used;
7. The spatial resolution of position acquisition and of the movement of carriers or racks, as also of common laboratory articles, such as microplates and sample tubes, is significantly higher than in systems known in prior art;
8. It is not necessary to know the current position of the local exciter of the RFID tags as in systems known in prior art. The current position of a local exciter can be acquired automatically;
9. The use according to the invention of RFID labels (tags) is fully compatible with the parallel or simultaneous use of other identification systems, e. g. bar-codes.

Figure 2:
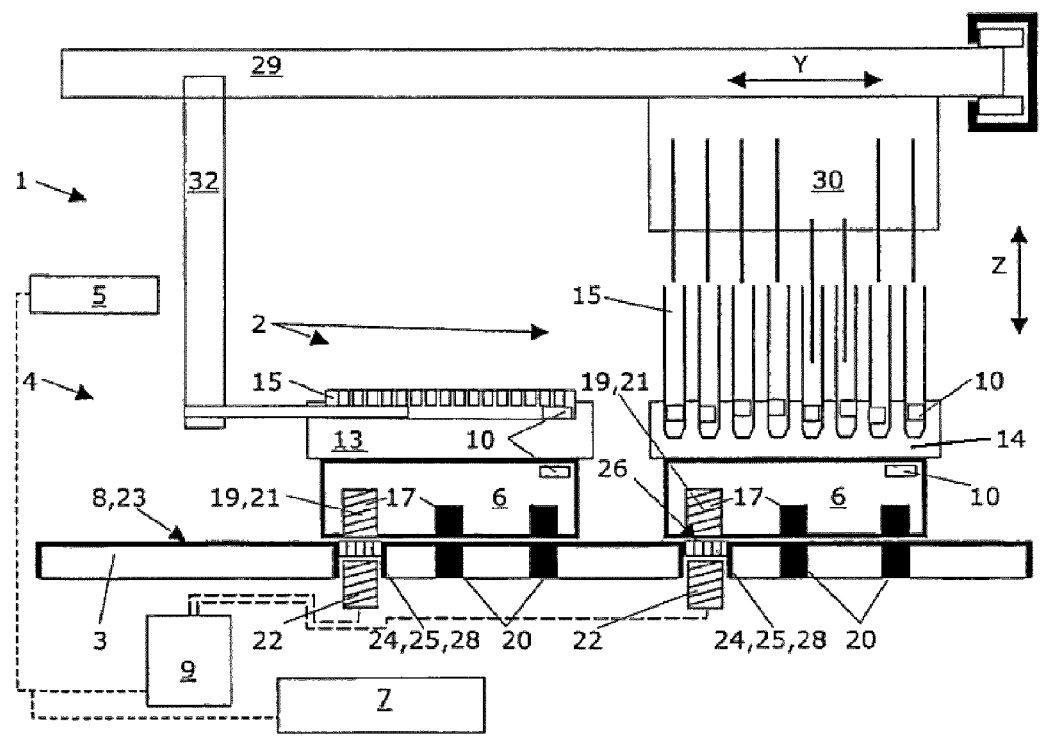

The system or procedure according to this invention will now be described in greater detail with reference to schematic example drawings. These drawings may not be taken to restrict the scope of the present invention in any way. They show the following:

FIG. 1 top view of a work table of a laboratory apparatus, in which the system according to the invention is embodied with first and second grid variants according to a second form of embodiment;

FIG. 2 a vertical partial cross-section through the work table of the laboratory apparatus according to FIG. 1;

FIG. 3A a vertical partial cross-section through a local unit, embodied as a microplate carrier;

FIG. 3B a vertical partial cross-section through a local unit, embodied as a rack for sample tubes;

FIG. 4A a first communication diagram according to the invention (I);

FIG. 4B a second communication diagram according to the invention (II).

In a first form of embodiment according to the invention, a system 1 is provided which serves to identify and locate or track objects 2 which can be positioned on a work table 3. The work table 3 is part of a laboratory apparatus 4 in the form of a robotic sample processor (RSP), such as a pipetting apparatus for the take-up and release of liquids or a dispenser for metering liquids. The system 1 comprises at least one central transmitter 5 which is capable of emitting and receiving radio frequency (RF) signals. The central transmitter 5 of the first form of embodiment is also capable of converting RF signals received and relaying these converted signals to a computer 7 of the system 1. The system 1 comprises at least one local unit 6, which is mounted on a surface 8 of the work table 3 and which is capable of receiving and sending RF signals. The system 1 comprises radio frequency identification (RFID) tags to be affixed to the local unit 6 and the articles of laboratory ware 15 to be identified and located or tracked. The system 1 (as already remarked) comprises a work table 3 of a laboratory apparatus 4 as well as a computer 7 which can be connected to the laboratory apparatus 4 and which is connected to the central transmitter 5 via an interface. The computer 7 is capable of communicating with the central transmitter 5, of processing signals received from the latter and of calling up selected RFID tags 10 via the central transmitter 5. With this minimum of equipment, the presence of an individual article of laboratory ware 15 (e. g. a microplate) as well as the current location and movements of articles of laboratory ware 15 (e. g. sample tubes) can be determined, this laboratory ware 15 being placed on an individual carrier 13 or rack 14 so that it can be picked up. Communication between the central transmitter 5 and the RFID tags 10 can take place according to this first form of embodiment (not shown in detail), using RF signals only (according to communication diagram I in FIG. 4A). The functioning of this first, simple form of embodiment will become clear to any specialist after reading the following description of the second form of embodiment (which is also shown in the drawing). It will be observed that RFID tags 10 that are enabled to send more complex information must be used for this first form of embodiment; such more complex information comprising at least a unique identification and/or data giving the type of laboratory ware 15 to which they are affixed. With this minimum level of equipment, information about the identity and number of articles of laboratory ware 15 and about the position of an individual microplate can be obtained. However, without the employment of additional means, such as light barriers in insertion positions, only identification can be obtained, but not the location of a plurality of articles of laboratory ware 15 (e. g. sample tubes).

A further developed and therefore preferred second form of embodiment is shown in FIGS. 1 and 2. FIG. 1 shows a top view of a work table 3 of a laboratory apparatus 4 in which the system 1 according to the invention is embodied with a first and second grid variant corresponding to a second form of embodiment of the invention. The laboratory apparatus 4 shown takes the form of a robotic sample processor (RSP) and comprises the work table 3 and robot arms 29 to move a pipetting device 30 across essentially the whole of the working area of the work table 3. The laboratory apparatus 4 takes the form of a pipetting apparatus for the take-up and release of liquids or a dispenser for metering liquids. Other sample processors comprise stackers or incubators for articles of laboratory ware 15 such as microplates; weighing systems for articles of laboratory ware 15; centrifuges for articles of laboratory ware 15 such as microplates or sample tubes; scanning or imaging devices and all other instruments for performing checks or manipulations on samples. The work table 3 illustrated extends in a longitudinal (X) and lateral (Y) direction, these two directions including a right angle. Different working or storage zones of a given workstation or even different workstations can be connected together with one or more robotic handlers 32, such as, for example, plate-carrying robots (cf. FIG. 2) or other robotic transport devices, such as conveyor belt or rail systems, etc.

Objects 2 are or can be positioned on the work table 3 of the laboratory apparatus 4. In association with the present invention, such objects 2 include local units 6, which can be fastened to the surface 8 of the work table 3. The local units 6 are so designed that they can receive energy from activation units 9 (not shown in FIG. 1; cf. FIG. 2), emit radio frequency (RF) signals and call up and activate a number of radio frequency identification (RFID) tags 10 (cf. FIG. 2). Here, the local units 6 are incorporated in carriers 13. In connection with the present invention, such articles of laboratory ware 15 comprise containers for samples, such as fluid samples in sample tubes or in microplates of all possible dimensions (e.g. preferably microplates with 96, 384 or 1536 wells) and all possible volumetric capacities. The work table 3 of the laboratory apparatus 4 is equipped with at least one addressable activation unit 9 to activate the local unit 6 (not shown in FIG. 1; cf. FIG. 2). The work table 3 comprises a virtual grid 11 designed to divide the work table surface 8 into grid units 12. According to a first variant of the present invention, this grid 11 is a Cartesian coordinate system as marked out by the lines (see FIG. 1) that run through the centres of the arrangement of through-holes 24 reaching through the cover 23 of the work table 3. Should a virtual grid 11 be defined with smaller grid units 12, the distance between the through-holes 24 could be reduced. Alternatively, and according to a second variant, the grid 11 could be tilted with respect to the longitudinal side X and the lateral side Y of the work table 3. The angle of tilt of this second variant of the grid 11 should preferably equal 45°. According to a further alternative, the two variants of the grid 11 would be combined, as shown at top left in FIG. 1.

In a variation on the steel cover 23 with through-holes 24 shown so far, objects 2 can be positioned on a cover 23 made of plastic (or at least with a surface layer 27 of plastic) with or without translucent portions in place of the through-holes 24. Another possibility is the use of a cover 23 made of aluminium without through-holes 24. In any case, it is preferable that the surface 8 of the work table 3 should be made as smooth as possible so that the cleaning and disinfection operations attendant on the use of the work table 3 can be easily carried out. Preference is given to chemically inert materials for the surfaces 8 of the work table 3, such as steel, plastic or aluminium. Should plugs 25 be used, for example, to close the through-holes 24, or optically transparent portions 28 instead, it is preferable for the plug surface 26 or the surface of the optically transparent portions 28 to be flush with the surface 8 of the work table 3 so that a smooth, flat work table surface 8 is obtained. Should a work table 3 with a completely flat upper surface be employed, the cover 23 of the work table 3 should preferably be transparent to all possible electromagnetic wavelengths used for activation of the local units 6.

FIG. 2 shows a vertical partial cross-section through the work table 3 of the laboratory apparatus according to FIG. 1. It shows a system 1 to identify, locate and track objects 2 that may be positioned on the work table 3 of a laboratory apparatus 4. This system 1 comprises at least one work table 3 of a laboratory apparatus 4, a central transmitter 5, at least one local unit 6, a computer 7, at least one addressable activation unit 9, RFID tags 10 and a grid 11 consisting of grid units 12.

Objects 2, articles of laboratory ware 15 (e.g. sample tubes or microplates) including carriers 13 or racks 14, are positioned on the work table 3 of this laboratory apparatus 4. RFID tags can be or already are affixed to these objects 2. By activation of these RFID tags 10, these objects 2 can be identified and their present position on the work table 3 can be located. If these objects 2 are identified and located before and after the movement of an object 2, all the movements of this object 2 on the surface 8 of the work table 3 can be tracked. In this way, all objects can be identified, located and tracked, because they carry activatable RFID tags 10 and because their position can be established in relation to the grid 11.

Simple RFID tags 10 can be enabled just to send a standardized RF signal. It is preferable, however, for the RFID tags 10 to be capable of sending an individual identification, e.g. in the form of a message showing the type of the object to be located. Particularly preferred, special RFID tags 10 send an individual (unique) identification which also gives the type and history of the sample contained in the article of laboratory ware 15 with this special tag 10. Specially preferred RFID tags 10 comprise all the characteristics of contemporary and future, commercially obtainable RFID tags. Especially interesting are rewritable RFID tags 10.

The work table 3 of the laboratory apparatus 4 comprises a grid 11 which divides up the surface 8 of the work table 3 into grid units 12 (cf. FIG. 1). The work table 3 also comprises transmitter elements 22 to transmit energy to the receiver elements 19 incorporated in the local units 6. These transmitter elements 22, by their position or their present arrangement below the surface 8 of the work table 3, define the grid intersection points of the grid 11.

The system 1 in the second form of embodiment (cf. first communication diagram I in FIG. 4A) comprises a central transmitter 5 which is connected to a computer 7 through an interface and is capable of transmitting and receiving radio frequency (RF) signals. The central transmitter 5 is also preferably enabled to control at least one local unit 6 located on the work table 3. According to the second form of embodiment, these local units 6 have the capability to be fixed to a surface 8 of the work table 3 and are adapted to the reception of energy from at least one activation unit 9. The central transmitter 5 is also able to convert the RF signals received and to relay these converted signals to a computer 7. The computer 7 can be connected to the laboratory apparatus 4 and is connected via an interface both to the central transmitter 5 and to activation units 9. The computer 7 is able to communicate with the central transmitter 5, to process signals received from the latter and to control selected activation units.

The fixing of the local units 6 to the surface 8 of the laboratory apparatus 4 should preferably be possible without making any alteration to the surface of the work table 3, that is to say without, for example, any notches, rails, studs or similar which might be present in or on the cover 23 of the work table 3.

Mounting of local units 6 on an essentially flat work table 3 is therefore preferably effected by means of positioning devices 17, which are part of the local units 6. These positioning devices 17 preferably take the form of magnets or magnetic devices 20, which may comprise permanent magnets and/or electromagnets. The positioning devices 17 can comprise a receiver element 19 and/or a micro-positioning element 21. The micro-positioning elements 21 may also be built into the local units 6 separately from the positioning devices 17 previously mentioned. The local units 6 are also capable emitting RF signals and of controlling and activating a certain number of RFID tags 10.

As described above, the laboratory apparatus 4 shown takes the form of a robotic sample processor (RSP) comprising the work table 3 and robot arms 29 with which a pipetting device 30 can be moved across essentially the whole of the working area of the work table 3. The work table 3 here extends in a longitudinal (X) and lateral (Y) direction, these two directions including a right angle (cf. FIG. 1). The pipetting device 30, or at least pipette needles or pipette tips fixed to the pipetting device 30, can be moved in a Z-direction, this Z-direction being essentially perpendicular to the work table 3 extending in a longitudinal (X) and lateral (Y) direction. Different working or storage zones of a given workstation or even different workstations can be connected together with one or more robotic manipulators 32, such as, for example, plate-carrying robots (cf. FIG. 2) or other robotic transport devices, such as conveyor belt or rail systems, etc.

The local units 6 are preferably incorporated in carriers 13 or racks 14. Each of the carriers 13 or racks 14 can be equipped to identify an individual article of laboratory ware 15 placed in this carrier 13 or rack 14 with at least one antenna 16. The at least one addressable activation unit 9 provided by the system 1 is brought into use via the transmitter elements 22 to activate the local unit 6.

The system 1 in the second form of embodiment (cf. communication diagram II in FIG. 4B) also comprises a central transmitter 5 which is connected to the computer 7 via an interface and is enabled to receive RF signals from at least one local unit 6 on the work table 3. In addition, the central transmitter 5 can receive RF signals from the RFID tags 10 fixed to the articles of laboratory ware 15. These local units 6 can be fastened to the surface 8 of the work table 3 and can draw energy from the activation units 9. When this occurs, the energy withdrawal by the local units 6 is preferably combined with identification of the local units 6.

Identification of a specific local unit 6 can be performed by establishing the presence of this local unit 6 on the basis of its energy extraction at a particular position on the grid 11. In addition, an individual identification is performed, this local unit 6 overlaying a modulated frequency on the electrical circuit through which energy reaches this local unit 6 via the transmitter element 22 and the receiver element 19. This frequency modulation should preferably be typical for a specific place on the grid 11.

As an alternative, the identification of a specific local unit 6 can be effected by the emission of RF signals generated by an RFID tag 10 affixed to this local unit 6. In this case, the RFID tag 10 is activated via the transmitter element 22 and the receiver element 19, these being in operating contact at a particular place on the grid 11, and the receiver element 19 being electrically connected to the RFID tag 10 of the local unit 6. An integrated switch 18 is preferably provided, with which the activation energy to be supplied to the RFID tag 10 of the local unit 6 is controlled.

FIG. 3A shows a vertical partial cross-section through a local unit 6 which is made in the form of a carrier 13 for a microplate. The local unit 6 again comprises positioning devices 17, as shown in FIG. 2, and as described above, in the form of magnets or magnetic devices 20. The positioning devices 17 here comprise a receiver element 19 and two magnetic devices 20.

The receiver element 19 takes the form of an induction coil which can be activated by an electromagnetic field of the transmitter element 22, the transmitter element 22 taking the form of an electromagnetic coil (not shown in detail). Each transmitter element 22 is arranged under the surface 8 of the work table 3 and in a position defined with respect to the grid 11. When the receiver element 19 of a local unit 6 is arranged in register with a transmitter element 22 (cf. FIG. 2), the electromagnetic field of the transmitter element 22 generates a current in the receiver element 19 by electrical induction. For this reason, there is no need to provide any sockets for the supply of electric current to the local units 6, so the surface 8 of the work table 3 can be kept flat. Of course, the cover 23 of the work table 3, or at least the plug 25 that closes the through-holes 24, must be permeable to the magnetic field of the transmitter element 22.

As an alternative, the receiver element 19 can take the form of an optical element able to receive light energy and convert it into electrical energy. In this case, the transmitter element 22 arranged under the cover 23 of the work table 3 and in a position defined with respect to the grid 11 takes the form of an optical element, e. g. a high-performance laser diode. Of course, the cover 23 of the work table 3, the surface layer 27 or at least the plug 25 that closes a through-hole 24, must be translucent to the light emitted by the transmitter element 22.

The receiver element 19 is in any case preferably connected to an integrated switch 18, to which an antenna 16 is connected. This antenna 16 is so arranged that if, for example, a microplate with an RFID tag 10 affixed to it is placed on a carrier 13, the antenna 16 will be in close proximity to the RFID tag of the article of laboratory ware 15. For this reason, for activation of the receiver element 19 surrounding this carrier 13, even weak RF signals are sufficient for the exclusive activation of the RFID tag 10 of the article of laboratory ware 15 received by the carrier 13.

FIG. 3B shows a vertical partial cross-section through a local unit 6 made in the form of a rack 14 for sample tubes. The local unit 6 comprises positioning devices 17, shown in FIG. 2 and described above in the form of magnets or magnetic devices 20. The positioning devices 17 here comprise a receiver element 19 and two magnets 20. The receiver element 19 is again preferably connected to an integrated switch 18, which is connected to a number of antennae 16. The antennae 16 are so arranged that, should a number of sample tubes with RFID tags 10 affixed to them be placed into the rack 14, they are positioned in close proximity to the positions of each of the RFID tags 10 of these articles of laboratory ware 15. For this reason, weak RF signals generated by activation of the receiver element 19 of the rack 14 are sufficiently strong to activate just those RFID tags 10 of the articles of laboratory ware 15 that are arranged on this rack 14. The integrated switch 18 preferably enables selection of specific sample tubes.

For unambiguously establishing the present position of the articles of laboratory ware 15, that is to say, of the RFID tags 10 affixed to these articles of laboratory ware 15, it is absolutely essential that only one specific, individual RFID tag 10 is addressed and activated by an antenna 16. Normally, the close proximity of an individual RFID tag 10 and the antenna 16 designated for its activation ensure reliable transmission of the RF signal to this selected RFID tag 10, so that none of the other RFID tags 10 present recognizes this transmission. Additional screening of the individual RFID tags 10 and/or antennae 16 (e. g. by the use of pieces of aluminium foil) can further improve reliability of reception.

In the interests of simplification of the drawings, only four sample tubes are shown in FIG. 3B. However, any conventional number, such as 1, 2, or a multiple of these, such as 8, 12, 15, 24 or n, of sample tubes can be received by correspondingly designed racks 14. The micro-positioning elements 21 can be incorporated in the local units 6 as part of the receiver element 19. In order to be able to detect even small deviations from the ideal position, specially arranged magnets or light barriers are preferably provided. Any specialist will know how to select suitable types of such micro-positioning elements 21 (not shown) so that sensitive detection of deviations from the exact aligned position between the receiver element 19 and the transmitter element 22 can be performed.

The micro-positioning elements 21 can be incorporated in the local units 6 as part of the magnetic device 20. In order to be able to detect even small deviations from the ideal position, specially arranged magnets are preferably provided. Any specialist will know how to select suitable types of such magnets (not shown) so that sensitive detection of deviations from the exact aligned position between the magnets 20 of the local unit 6 and the magnets 20 of the work table 3 can be performed.

The micro-positioning elements 21 can be incorporated in the local units 6 both separate from the receiver element 19 and also separate from the magnets 20. For these variants, light barriers (not shown) are specially preferred.

If RFID tags 10 are affixed to the local units 6, the latter are also able to send RF signals to the central transmitter 5. By the use of the antennae 16, the local units 6 are able to individually address and activate a number of selected RFID tags 10 of articles of laboratory ware 15 positioned on the carrier 13 of this local unit 6.

FIG. 4A shows a first communication diagram according to the invention (I). This communication diagram I is used for general identification, so that a list can be compiled that subdivides the objects 2 on the work table 3 of a laboratory apparatus 4 into classes with racks 14, articles of laboratory ware 15 and samples. The central transmitter 5 has the capability to transmit RF signals using a first communication channel (c1) and to receive RF signals using a second communication channel (c2).

In connection with the present invention, the term "communication channel" is to be understood to mean any possible path of any imaginable procedure for the transmission and/or reception of information. In connection with the present invention, the term "communication channel" may be understood to mean a special radio frequency, an allocated pair of cables, a special modulation schema (e. g. RF modulation, amplitude modulation), or a specific bandwidth. In FIG. 4A, two forms of communication channels are shown: the RF signals c1 and c2 and the cabling (double-ended arrow) that links the central transmitter 5 to the computer 7 via an interface.

FIG. 4B shows a second communication diagram according to the invention (II). This communication diagram (II) is used for individual identification of the objects 2 present on the work table 3 of a laboratory apparatus 4, such as racks 14, articles of laboratory ware 15 and samples. The central transmitter 5 has the capability to transmit RF signals using the second communication channel c2 and to receive signals using a third communication channel (c3). The third communication channel c3 comprises a first part that links the computer 7 to an activation unit 9, a second part (c3a) that connects the activation unit 9 to at least one transmitter element 22 and a third part (c3b) that links a local unit 6 to at least one article of laboratory ware 15.

In FIG. 4B, a variety of types of communication channel are shown: the RF signals c2 and c3b; the directional signals in the cabling between the activation unit 9 and the transmitter elements 22, the activation of the receiver element 19 via the transmitter element 22 and the cabling (double-ended arrow) that links the central transmitter 5 to the computer 7 through an interface. In addition, the wiring between a local unit 6 and its antennae 16 is depicted, as well as the wiring between the receiver element 19 and the RFID tag 10 (cf. also (t) in FIG. 4) of the local unit 6.

The RFID tags 10 of the local unit 6 take the form of local transmitter/receivers which are enabled to receive the c1 RF signals of the first communication channel (cf. FIG. 4A), to convert these signals into corresponding c2 RF signals of the second communication channel and to transmit these c2 RF signals of the second communication channel to the central transmitter 5.

The local units 6 are preferably also enabled to be supplied with current via the transmitter element 22 and to emit c2 RF signals with an RFID tag 10 affixed to the local unit 6. The local units 6 are also preferably enabled to be activated via the transmitter element 22 and to transmit c3b signals via an antenna 16 to an RFID tag 10 affixed to an article of laboratory ware 15 that has been received in a rack 14. As regards this RFID tag 10, it has the capability to transmit c2 RF signals to the central transmitter 5. Each RFID tag 10 can be a passive RFID tag 10, receiving c1 RF signals on the first communication channel and c3b signals on the third communication channel as well as transmitting c2 RF signals on the second communication channel.

The transmitter element 22 can be recognized by the computer 7 if the third communication channel c3 is used in reverse direction between the transmitter element 22, the activation unit 9 and the computer 7. The receiver element 19 of each individual local unit 6 is individually addressable via a transmitter element 22 arranged under the work table 3 and in register with a grid unit 12. As regards the transmitter elements 22, these can be individually controlled and activated via the activation unit 9.

There are several preferred variants in the way a work table 3 can be constructed:

A first variant comprises a steel cover 23 with through-holes 24 arranged in an array and corresponding to the grid 11. In each case, there is a transmitter element 22 in register under a plug 25 closing this through-hole 24. This is done in such a way that the surface 26 of each plug 25 is flush with the surface 8 of the work table 3.

A second variant of the work table 3 comprises a plastic surface layer 27 on the surface 8, this surface layer 27 displaying optically transparent portions 28 in an array corresponding to the grid 11. In each case, a transmitter element 22 is arranged below and in register with an optically transparent portion 28.

A third variant of the work table 3 comprises an aluminium cover 23. The transmitter elements 22 are arranged beneath the aluminium cover. Each of the transmitter elements 22 is equipped as an electromagnetic transmitter, the aluminium cover being permeable to the magnetic field of the transmitter elements 22.

The application of the preferred procedure according to the invention for identifying objects 2 arranged on a work table 3 of a laboratory apparatus 4 or a system 1 serves to obtain a first set of general information and comprises the following procedural steps:

a) All objects 2 for identification are preferably equipped with radio frequency identification (RFID) tags. It is not absolutely necessary to provide the local units 6 with RFID tags 10, because these local units 6 can also be addressed via the transmitter element 22/receiver element 19 combination, using the third communication channel c3a (cf. FIG. 4B). It is however essential for each article of laboratory ware 15, in the form of sample tubes or microplates, for example, to be fitted with an RFID tag 10.

b) Carriers 13 or racks 14 are placed on the surface 8 of the work table 3. These carriers 13 or racks 14 are designed for the reception of articles of laboratory ware 15. Such articles of laboratory ware 15 can be positioned on the carriers 13 or the racks 14, as the case may be. Positioning of the carriers 13, which in all cases comprise a local unit 6, can be performed manually or by a robot of the laboratory apparatus 4. Positioning of the articles of laboratory ware 15 can similarly be performed manually or by an automated operation by a robot of the laboratory apparatus 4.

c) An order for the emission of a general radio frequency (RF) signal is sent by a computer 7 to a central transmitter 5 connected to it via an interface (see double-ended arrows in FIG. 4A). This order can be initiated by an operator or by a program step in a corresponding computer program.

d) The required general RF signal is transmitted by the central transmitter 5, using a first communication channel c1. It is preferable to use an RF signal of a first frequency for this transmission.

e) The general RF signal transmitted in step d) is received by all the RFID tags 10 affixed to the objects 2. Because at least every article of laboratory ware 15 is equipped with such an RFID tag 10, all these RFID tags 10 affixed to these articles of laboratory ware 15 are activated by the reception of this general signal. If the local units 6 are also fitted with RFID tags 10, then these RFID tags 10 also receive the general RF signal and are also activated. The RFID tags 10 are preferably designed to receive RF signals on a first frequency.

f) The RF signal received by the RFID tags 10 in step e) is converted and the converted RF signal is transmitted by the RFID tags 10 to the central transmitter 5 using a second communication channel c2 (cf. FIG. 4A). Any conceivable types of anti-collision protocol can be employed, so the RF signal from the RFID tags 10 may, for example, be transmitted on a second frequency with a wavelength different from the first frequency.

According to the capacities of the RFID tags 10 employed, the RF signal transmitted to the central transmitter may just be a simple signal, which merely communicates the presence of this RFID tag 10 and hence the presence of a local unit 6 or an article of laboratory ware 15. It is preferable, however, if the RFID tags 10 used to transmit the RF signal are enabled to give some information regarding the type of objects 2 to which they are affixed. Particularly preferred is the transmission of supplementary information regarding the type and history of the sample or samples contained in the article of laboratory ware 15 in question. Specially preferred RFID tags 10 comprise all the characteristics of contemporary and future commercially obtainable RFID tags 10; among these, rewritable RFID tags 10 are of particular interest.

g) The RF signals sent by the RFID tags 10 in step f) are received by the central transmitter 5.

h) The central transmitter 5 converts the signals received in step g) into digital data. The central transmitter 5 should preferably have the capability to send RF signals of a first frequency and receive RF signals of a second frequency.

i) The central transmitter 5 sends the digital data converted in step h) to the computer 7.

j) The computer 7 receives the digital data transmitted by the central transmitter 5 in step i) and processes them. According to the information conveyed by the central transmitter 5, i.e. originating from the RFID tags 10, the computer establishes the number of RFID tags 10 or objects 2 present on the work table 3 of the laboratory apparatus 4. This counting is considerably easier to perform if an anti-collision protocol is used. Such an anti-collision protocol may consist, for instance, in transmitting the RF signals from the RFID tags 10 to the central transmitter 5 sequentially (and not in parallel), or in conveying at least the corresponding digital data from the central transmitter 5 to the computer 7 sequentially. Should the RFID tags 10 transmit additional information, the computer 7 has the capability to compile a list of all the objects 2 present on the work table 3. In a most preferred version of the procedure, the computer would even produce a list of all the objects 2 and all the samples present on the work table.

Use of the preferred procedure for the identification and location of objects 2 positioned on the work table 3 of a laboratory apparatus 4 to locate these objects 2 also comprises the following procedural steps:

k) An order to deliver energy to a selected local unit 6 is sent according to the invention by the computer 7 to the activation unit 9 of the system 1. Here again, this order may be initiated by an operator or by a program step in the corresponding computer program. The activation unit 9 is connected to the computer 7 via an interface and for this purpose a third communication channel c3a is used. This communication channel c3a takes the form of cabling that links the activation unit 9 to all the transmitter elements 22 of the work table 3. By means of the individual cabling between the transmitter elements 22 and the activation unit 9, each transmitter element 22 can be individually supplied with energy. However, any desired selection of transmitter elements 22, or all of them, can be actuated simultaneously.

l) The selected local units 6 supplied via the transmitter elements 22 arranged under the cover 23 of the work table 3 of the laboratory apparatus 4 according to the invention are supplied with energy by these transmitter elements 22. This is made possible by a transmitter element 22 taking the form of an electromagnetic coil or an optical element, for example.

m) The local unit 6 activated in step l) transmits, through one or more antennae 16, c3b RF signals to the RFID tags 10 affixed to articles of laboratory ware 15 received in the carrier 13 or rack 14 of the local unit 6. For each sample tube inserted in the rack 14 of the local unit 6, preferably only the RFID tag 10 closest to an antenna 16 currently transmitting is activated. For this reason, when the antennae 16 of a local unit 6 are excited sequentially, each single RFID tag 10 of the sample tubes can be activated individually. Because the integrated switch of the local unit 6 knows the transmission point of the antenna 16, each RFID tag 10, together with its individual sample in a sample tube, can be identified and located or referenced. For microplates positioned on a carrier 13 of a local unit 6, a corresponding equivalent procedure can be employed. This also applies if more than one microplate is positioned on a carrier 13. The c3b RF signal is preferably a first frequency RF signal, the same as the RF signals emitted by the central transmitter 5.

n) The RFID tag 10 affixed to an article of laboratory ware 15 that is closest to the transmitting antenna 16, receives the c3b RF signal of the corresponding local unit 6. Normally, the close proximity of an individual RFID tag 10 to a selected antenna 16 designated for its activation will be sufficient to ensure transmission of the RF signals exclusively to this RFID tag; none of the other RFID tags 10 also present on this carrier 13 recognizes this signal transmission. Additional screening of the individual RFID tags 10 and/or antennae 16 (e. g. by the use of pieces of aluminium foil) can further improve reliability of reception. In consequence, only one specific RFID tag 10 is selectively and individually activated by the reception of these RF signals, and this RFID tag 10 converts the c3b RF signals received in step m) into c2 RF signals of the second communication channel and transmits them to the central transmitter 5. The c2 RF signal preferably displays a second frequency corresponding to the second frequency of the RF signals transmitted by the RFID tags 10.

o) The central transmitter 5 receives these c2 RF signals transmitted by an RFID tag 10 in step n) and converts these RF signals into digital data, which it thereupon transmits to the computer 7. This data transfer is carried out over the cable connection that links the central transmitter 5 to the computer 7 via an interface.

p) The computer 7 analyses the digital data received in step o) and establishes an X/Y distribution map of the articles of laboratory ware 15 present on the work table 3. The X/Y coordinates on the work table 3 are determined by the present position of the local unit 6 positioned on a grid unit 12 of the grid 11. Individual Z values (or height values) are preferably added on the X/Y distribution map of the present locations of the articles of laboratory ware 15 positioned on a local unit. If carriers 13 are used, taking the form of "hotels" receiving stacks of microplates, each individual Z position, or each individual Z value for each individual article of laboratory ware 15, is preferably recorded in the same way on the X/Y distribution map. To enable such acquisition of Z values, antennae 16 (and where necessary, screens) are provided on each story, or at each Z level, where a microplate can be inserted. Identification of these local units 6 is carried out by selective addressing via the activation unit 9, or by sequential communication between the activation unit 9 and some or all of the local units 6, via the communication channel c3a (cf. FIG. 4B). As a variant on this method, the local units 6 can be addressed by the central transmitter 5, if an RFID tag 10 has been affixed to the latter. If this is the case, such an RFID tag 10 should preferably be so designed as to be capable also of sending information relating to the type of the local unit 6 to which it is affixed.

Use of the procedure according to the invention for the identification and location of objects 2 positioned on the work table 3 of a laboratory apparatus 4 for the purpose of obtaining information relating to changes of position or movements comprises the repetition of some or all of the procedural steps a) to p) as defined above.

Activation of the selected local units 6 with a transmitter element 22 arranged under the work table 3 of the laboratory apparatus 4 can be performed with any system capable of conveying energy through the surface 8 of the work table 3. Preferred systems for such energy transfer include the use of electrical induction, capacitative coupling or optical transfer.

Similarly, the RFID tags 10 affixed to the articles of laboratory ware 15 may be excited by means of any system that is capable of supplying energy targeted on the individual position occupied by such an article of laboratory ware 15. Preferred such energy transfer systems include the use of RF signals, electrical induction, capacitative coupling or optical transfer (e. g. in the form of visible or infrared light). Specially preferred for optical transfer is the use of focused infrared light which strikes a photocell integrated in or at least functionally connected to the RFID tag. One optical element for each article of laboratory ware 15 to be excited, such as high-performance laser diodes or individual light conductors leading to the individual articles of laboratory ware, enables a local unit to transfer energy to such optoelectric RFID tags. If light conductors are used for several articles of laboratory ware 15 positioned on a local unit 6, an individual light wavelength of excitation light can be allocated to each light channel.

Advantages of the use of light energy, especially focused infrared light, include significantly easier screening against RF signals of articles adjacent to this article of laboratory ware 15 that are not to be excited. Mixed variant methods of energy transfer to local units 6 and to RFID tags 10 on articles of laboratory ware 15 may also be provided, among which, for example, the local units 6 may be activated by electrical induction, but the RFID tags 10 of the articles of laboratory ware 15 by light, preferably focused infrared light.

As an alternative to the forms of embodiment presented so far, light (e. g. in the form of visible or infrared light) can also be used to trigger a switching pulse. In this special form of embodiment, energy transfer is performed by means of electrical induction or RF signals. An individual light pulse is preferably emitted for an RFID tag to be activated and detected by a corresponding sensor linked to the RFID tag. This has the advantage that a common energy source can be ensured and that, despite individual response through one or more RFID tags addressed, no complicated screening protocols need be provided.

To keep the local units 6 in their positions on the surface 8 of the work table 3 (but without the use of mechanical retaining means such as rails, notches, studs or plugs), magnetic devices 20 (see FIGS. 2 and 3) are employed. In this way, carriers 13 or racks 14 can also be held in position on the work table 3. To define the exact position of the local units 6, which are designed to comprise carriers 13 or racks 14 to receive articles of laboratory ware 15, specially designed transmitter elements 22 and receiver elements 19 can be used as micro-positioning elements 21. For this purpose, transmitter and receiver elements are selected that can detect spatial differences of millimeter magnitude or less. Such high resolution can only be obtained through the use of light barriers or an inductive system. The inductive system will then comprise coils for the transmitter elements 22 and the receiver elements 19 such that they display very narrow overlap zones of electromagnetic field lines when these elements are arranged one above the other in register on the work table 3 of a laboratory apparatus 4. The activation unit 9 can easily detect faulty positioning when it communicates with the local units 6: even the slightest deviations are detected by the fact that the energy intake of the local units 6 is significantly reduced.

Such micro-positioning elements 21 can form part of the transmitter elements 22 and the receiver elements 19. They can also be arranged as part of the magnetic devices 20, or in a different arrangement, separate from the other systems in the local units 6 and below the surface 8 of the worktables 3.

In each case, the exact position of the micro-positioning elements 21 is preferably defined in relation to the grid 11 and the grid units 12.

If the computer 7 is provided with the corresponding software, it has the capability to draw up detailed surface maps and lists of the objects 2, i.e. the local units 6, carriers 13 and racks 14 and similarly the articles of laboratory ware 15 and samples present on the work table 3 of a laboratory apparatus 4. Such a laboratory apparatus 4 may be a single instrument or a part of a higher-ranking logistical system 31 for the handling or processing of samples, such as blood and other body fluids of humans or animals. Such higher-ranking logistical systems 31 can comprise all instruments and devices that are necessary for the processing, analysis, handling, transfer and storage of biological or chemical samples. The computer 7 preferably has the capability to supply or provide all the digital data relating to the identity and position of the objects 2 on the surface 8 of the worktables 3 to such higher-ranking logistical systems. Such a laboratory apparatus 4 can integrate the presentation of the present positions and movements of individual samples on the work table 3 into a higher-ranking logistical system for the processing and analysis of desired samples. Several different working or storage zones of a given workstation or even different workstations can be connected together with one or more robotic manipulators 32, such as, for example, plate-carrying robots (cf. FIG. 2) or other robotic transport devices, such as conveyor belt or rail systems, etc.

The reference symbols designate corresponding elements in all the figures, even if these are not expressly described. All reasonable combinations of the characteristics shown in the figures or described constitute part of the present invention. A diversity of commercially obtainable RFID tags shows a complete range of data storage facilities, identifications, frequency ranges, magnitudes, spatial operating zones and communication protocols, including anti-collision protocols. The present invention makes use of such RFID tags; the RFID tags, however, do not constitute part of the invention. For this reason, the present invention is not restricted to a particular type of RFID system or one RFID solution.

In a variant on the forms of embodiment of the present invention presented so far, in which specific addressees can be targeted for excitation, provision can also be made for simultaneous excitation of all the RFID tags 10 within range, but for a specific selection (or even all with a single exception) to be subjected to electronic jamming, so that they are prevented from emitting a response. Negative selection by interference has the advantage that jamming signals can be more easily emitted or transmitted and more accurately targeted than is possible with excitation. Any possible responses from RFID tags are suppressed by targeted jamming. It is also possible to use the communication channels, especially c3a and c3b, in reverse direction to identify the RFID tags 10 addressed (cf. FIG. 4B). To the specialist, reasonable combinations of the characteristics of the present invention disclosed here fall within the scope of the invention.

The invention claimed is:

1. A system (1) to identify and locate objects (2), the system (1) comprising:
   radio frequency identification (RFID) tags (10) to be affixed to objects (2) that are to be identified and to be located, wherein the RFID tags are configured to receive and to transmit signals;
   a carrier (13) or racks (14) to accommodate objects (2) that are to be identified and located;
   a plurality of antennae (16) to transmit signals to the RFID tags that are to be located;
   at least one unit comprising a receiver element (19) and a transmitter element (22), the receiver element (19) is connected to the antennae (16) and activates a transmitting antenna (16), so that a single RFID tag (10) is activatable, which is in close proximity to the transmitting antenna (16) activated by the receiver element (19), and the transmitter element (22) transmits energy to the receiver element incorporated in the unit;
   a computer (7); and
   a central transmitter (5) to at least transmit signals to at least one transmitter element (22), to receive signals from the RFID tags (10), and to convert signals received and transfer the converted signals to the computer (7);
   the computer (7) comprising a software for providing digital data relating to the identity and position of the objects (2), the software processing signals received from the central transmitter (5);
   wherein the system (1) is accomplished as a laboratory system comprising a laboratory apparatus (4) having a laboratory work table (3), wherein articles of laboratory ware (15), the carrier (13) or the rack (14) that are to be identified and to be located, are positionable on a surface (8) of the laboratory work table (3); the laboratory work table (3) comprising a virtual grid (11) which is designed to divide the surface (8) of the laboratory work table (3) into grid units (12);
   wherein the at least one unit is accomplished as a local unit (6) which comprises at least one receiver element (19) and which is incorporated in the carrier (13) or rack (14);
   wherein the transmitter elements (22) are arranged below the surface (8) of the laboratory work table (3) in a defined position thus defining the grid intersection points of the grid (11);
   a receiver element (19) of a local unit (6) is arranged in register with and above a transmitter element (22), the transmitter element (22) transmitting energy through the laboratory work table (3) to the receiver element (19); and
   at least one antenna (16) is incorporated in a carrier (13) or a rack (14), so that a single RFID tag (10) of an article of laboratory ware (15), which is closest to an antenna (16) of the carrier (13) or rack (14) currently being activated by the receiver element (19) and thus currently transmitting, is individually activatable.

2. The system (1) according to claim 1, wherein the local unit (6) further comprises a positioning device (17) for the controlled positioning of the carriers (13) or racks (14) on the surface (8) of the laboratory work table (3).

3. The system (1) according to claim 1, wherein the positioning device (17) comprises a receiver element (19) or takes the form of a magnetic device (20).

4. The system (1) according to claim 1, wherein the laboratory system (1) comprises at least one activation unit (9) which activates the transmitter elements (22) and which is connected with the computer (7) and with the central transmitter (5).

5. The system (1) according to claim 1, wherein per local unit (6) a transmitter element (22) takes the form of an optical element which transmits light energy, wherein the corresponding receiver element (19) takes the form of an optical element able to receive the light energy and to convert it into electrical energy.

6. The system (1) according to claim 1, wherein per local unit a receiver element (19) takes the form of an induction coil, and a corresponding transmitter element (22) takes the form of an electromagnetic coil for activating the receiver element (19) by an electromagnetic field.

7. The system (1) according to claim 1, wherein for improving the reliability of reception of individual signals transmitted by an antenna (16) and received by a defined RFID-tag (10), the individual RFID tags (10) and/or the individual antennae (16) are screened from each other.

8. The system (1) according to claim 1, wherein the laboratory work table (3) comprises a steel cover (23) with through-holes (24) that are arranged in an array corresponding to the grid intersection points of the grid (11), wherein in each case there is a transmitter element (22) arranged in register with and under a plug (25), each plug (25) closing this through-hole (24), and wherein the surface (26) of each plug (25) is flush with the surface 8 of the laboratory work table (3).

9. The system (1) according to claim 1, wherein the surface (8) of the laboratory work table (3) comprises a plastic surface layer (27), which displays optically transparent portions (28) in an array corresponding to the intersection points of the grid (11), the transmitter elements (22) being arranged underneath this plastic surface layer (27).

10. The system (1) according to claim 1, wherein the laboratory work table (3) comprises an aluminium cover (23), with the transmitter elements (22) being arranged as an electromagnetic transmitter under this aluminium cover (23), said aluminium cover (23) being permeable to the magnetic field of the transmitter elements (22).

11. The system (1) according to claim 1, wherein the laboratory apparatus (4) is a robotic sample processor (RSP).

12. The system (1) according to claim 1, wherein for optically exciting the RFID-tags (10), the local unit (6) is equipped with at least one optical transmission element for transmission of light signals, and the RFID-tags (10) comprising or being functionally connected to a photocell to receive light energy.

13. Application of the system (1) according to claim 1, wherein the digital data corresponding to the positions of the objects (2) on surface of the laboratory work table (3) are made available to higher-ranking logistical systems.

14. A method of identifying and locating objects (2) of a laboratory system (1), comprising the following steps:
providing radio frequency identification (RFID) tags (10) to objects (2) that are to be identified and to be located, wherein the RFID tags are configured to receive and to transmit signals;
providing carrier (13) or racks (14) to accommodate objects (2) that are to be identified and located;
providing a plurality of antennae (16) to transmit signals to the RFID tags that are to be located;
providing at least one unit comprising a receiver element (19) and a transmitter element (22), wherein the receiver element (19) is connected to the antennae (16) and activates the antennae (16), so that a single RFID tag (10) is activated, which is in close proximity to a transmitting antenna (16) activated by the receiver element (19); and wherein the transmitter element (22) transmits energy to the receiver element (19) incorporated in the unit;
providing a computer (7) and a central transmitter (5), the central transmitter (5) at least transmitting signals to at least one transmitter element (22), to receive signals from the RFID tags (10), and to convert signals received and transfer the converted signals to the computer (7); wherein the computer (7) comprises a software for providing digital data relating to the identity and position of the objects (2), the software processes signals received from the central transmitter (5);
wherein the system (1) is accomplished as a laboratory system comprising a laboratory apparatus (4) having a laboratory work table (3), wherein articles of laboratory ware (15), the carrier (13) or the rack (14) that are to be identified and to be located, are positioned on a surface (8) of the laboratory work table (3), and wherein the laboratory work table (3) comprises a virtual grid (11) which divides the surface (8) of the laboratory worktable (3) into grid units (12);
wherein the at least one unit is accomplished as a local unit (6) which comprises at least one receiver element (19) and which is incorporated in the carrier (13) or rack (14);
wherein the transmitter elements (22) are arranged below the surface (8) of the laboratory work table (3) in a defined position thus defining the grid intersection points of the grid (11);
a receiver element (19) of a local unit (6) being arranged in register with and above a transmitter element (22), the transmitter element (22) transmitting energy through the laboratory work table (3) to the receiver element (19); and
at least one antenna (16) being incorporated in a carrier (13) or a rack (14), so that a single RFID tag (10) of an article of laboratory ware (15), which is closest to an antenna (16) of the carrier (13) or rack (14) currently being activated by the receiver element (19) and thus currently transmitting, is individually activatable.

15. The method according to claim 14, wherein to track objects (2), single RFID-tags (10) are activated and the transmitted data are processed by the computer (7) before and after the movement of an object (2).

16. The method according to claim 14, wherein the activation of the receiver element (19) is performed by employing electrical induction or optical excitation.

17. The method according to claim 14, wherein positioning devices (17) are used to position carrier (13) and/or racks (14) on the surface (8) of the laboratory work table (3).

18. The method according to claim 14, wherein the computer (7) comprises a software enabling the computer (7) to draw up surface maps and lists of the objects (2), which are present on the work table (3).

19. The method according to claim 14, wherein the digital data corresponding to the positions of the objects (2) on surface of the laboratory work table (3) are made available to higher-ranking logistical systems.

* * * * *